United States Patent [19]

Cosman

[11] Patent Number: 4,966,597
[45] Date of Patent: Oct. 30, 1990

[54] THERMOMETRIC CARDIAC TISSUE ABLATION ELECTRODE WITH ULTRA-SENSITIVE TEMPERATURE DETECTION

[76] Inventor: Eric R. Cosman, 872 Concord Ave., Belmont, Mass. 02178

[21] Appl. No.: 267,211

[22] Filed: Nov. 4, 1988

[51] Int. Cl.⁵ ............................................. A61B 17/32
[52] U.S. Cl. ..................................................... 606/50
[58] Field of Search ...................... 128/303.13–303.17, 128/736, 786; 606/31, 41, 50

[56] References Cited

U.S. PATENT DOCUMENTS

| | | | |
|---|---|---|---|
| 2,888,928 | 6/1959 | Seiger | 128/303.17 |
| 3,920,021 | 11/1975 | Hiltebrandt | 128/303.17 |
| 4,051,855 | 10/1977 | Schneiderman | 128/303.14 |
| 4,311,143 | 1/1982 | Komiya | 128/303.15 |
| 4,411,266 | 10/1983 | Cosman | 128/736 |
| 4,532,924 | 8/1985 | Auth et al. | 128/303.17 |
| 4,682,596 | 7/1987 | Bales et al. | 128/303.17 |
| 4,796,640 | 1/1989 | Webler | 128/736 |

Primary Examiner—Max Hindenburg
Attorney, Agent, or Firm—Richard J. Birch

[57] ABSTRACT

This invention relates to the construction of a cardiac ablation electrode with a thermosensing detector at one or more positions in the distal tip. The distal tip is uninsulated in contrast to the rest of the flexible length of the electrode to enable radiofrequency (rf) potential to be applied there. This rf potential causes heating of cardiac tissue when the catheter electrode is inserted into the heart via venus pathways. A thermocouple sensor is embedded in the electrode tip with the detection wires running along the catheter to external apparatus for measurement to application of radiofrequency. The thermocouple sensor is integral and at the surface of the distal electrodes for true surface temperature recording with fast response.

4 Claims, 1 Drawing Sheet

THERMOMETRIC CARDIAC TISSUE ABLATION ELECTRODE WITH ULTRA-SENSITIVE TEMPERATURE DETECTION

BACKGROUND TO THE INVENTION

Radiofrequency lesioning electrodes have common application in neurosurgery. Examples of previous designs are illustrated in the present author's Pat. No. 4411266. Typically these electrodes consist of a cylindrical shaft insulated primarily over its entire length, with the exclusion of the exposed distal tip. Thermocouple or thermistor wires were located internal to the longitudinal shaft of the electrode, and a thermocouple of thermistor sensor is located at the electrode tip. Such electrodes are extremely important in neurosurgery and have been used effectively there.

The present invention is a new and unique electrode configuration involving a catherter-type electrode for use in cardiology. In that field, an objective is to destroy portions of the nerve-carrying cardiac tissue, such as the Hiss bundle, in which irregular pulse sources are present. Also in the case of cardiac infarction where disturbance of the normal trigger patterns and flow of electricity in the cardiac tissue is altered, radiofrequency heating or other heating methods for ablation of the trouble zones is indicated. Flexible cardiac catheters are well know in the field of cardiology. These catheters in some cases are insulated over their entire length and are directed through openings in the veins in the groin and work up to the cardiac region. Once there, the exposed metal tip of the electrode can be directed to a desired portion of the cardiac wall, and a pulse or continuous amount of radiofrequency energy can be delivered so as to heat the desired tissue. Here, as in the neurosurgical context, faithful reproduction of the tissue heating is important, and also rapid response to tell the surgeon about immediate changes of tissue is also of great importance.

Therefore, one object of this invention is to implement an embodiment of the flexible cardiac catheter for the purpose of cardiac tissue ablation by radiofrequency heating with ultra-fast faithful recording of temperature in the affected tissue.

DESCRIPTION OF THE INVENTION

Figure 1:
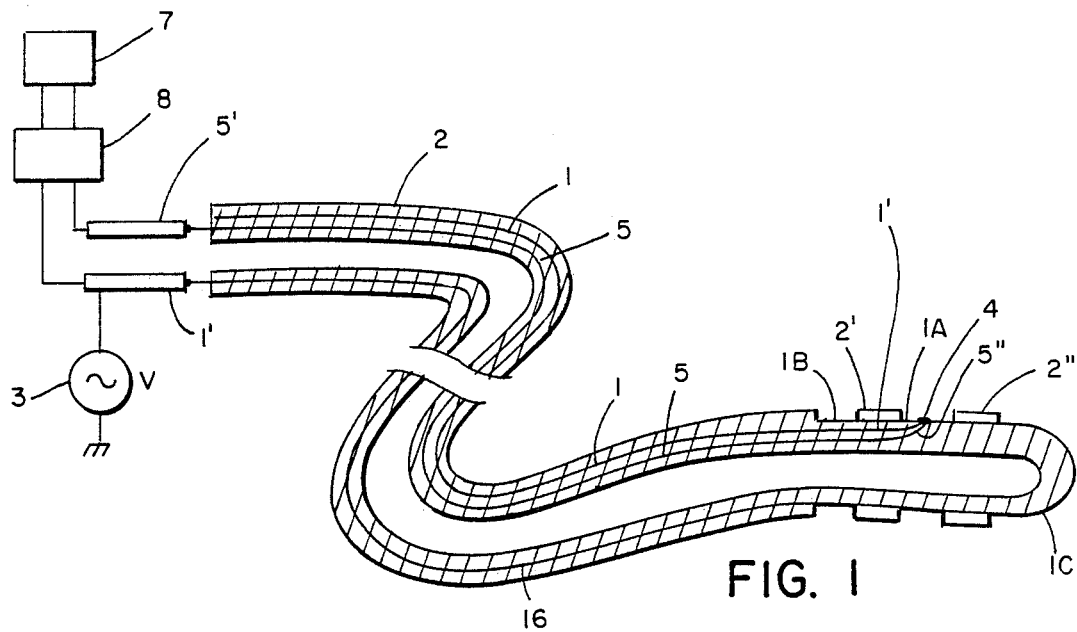
FIG. 1 shows a sectional view of one embodiment of the invention representing a flexible cardiac catheter.

Referring to FIG. 1, one sees the sectional view of a typical embodiment of the cardiac type catheter electrode. The electrode will have an insulative exterior 2, except for exposed tip regions 1A, 1B, and 1C. Other independent tip exposures could also be present. In the case of 1A, it is connected via a conductor indicated as 1 along the length of the catheter, and that in turn can be connected via contact 1' to a voltage source 3. Each of the surface electrodes 1A, 1B, and 1C can be independently connected to similar contacts as 1', or they can be all connected together. Typically such contacts in catheter electrodes can be used for recording or stimulation, and thus would be independent. For the purpose of illustration, we have focused on electrode surface 1A, which is connected electrically through conductor 1 to pin 1'. On surface 1A, we have connected the temperature-measuring conductor 5, which runs the length of the catheter to a junction element (for example thermocouple) with 5, which is designated as 5". The junction, therefore, consists of the end element 5" of the thermocouple element 5 and the end element surface 1A, which is electrically connected to 1. Elements 5 and 1 could, for example, be dissimilar metals such as copper and constantan or stainless steel and constantan to form a thermocouple junction. For instance, the conductor 1 could be a stainless steel, flexible, braided wire running the length of the catheter, and its end portion designated as 1' could attach to the surface element 1A, which could be a stainless steel ring. 1', which is the end portion of conductor 1 could then join to the end portion 5' of constantan element 5. This forms the junction 4. The junction 4 is on the surface and the exterior portion of the ring 1A and forms part of that external surface. Because of the dissimilar metals, there is a potential difference generated at junction 4 which reflects itself as a voltage difference between pins 1' and 5' which connect to stainless steel conductor 1 and constantan conductor 5 respectively. These contacts can then in turn be connected through a radiofrequency filter 8 to a thermometric measuring box circuitry 7 so that the temperature precisely at the surface 1A or correspondingly at the junction 4 is measured. Element 1 could be another material, such as copper, as long as it is dissimilar from the material 5 of the second conductor so that the thermocouple junction potential will be generated.

We have described the electrical and geometric configuration for only the electrical surface element 1A. Typically, the cardiac catheters have more surface elements, such as 1B and 1C and so on. Between them are insulative rings designated as 2' and 2" in the figure. Each of the electrical surfaces could have such surface thermocouple junctions, and there could be pairs of thermocouple connectors at the proximal end of the catheter, such as 1' and 5' for the surface 1A.

Figure 2:
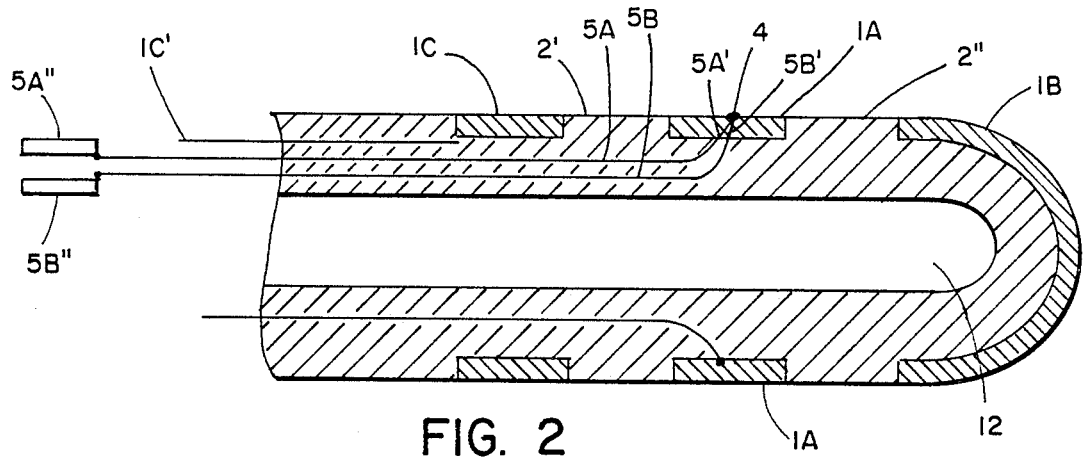
FIG. 2 shows a sectional view of the tip detail of the catheter showing the construction of the thermal sensor at one of the electrode surfaces.

FIG. 2 shows more detail in the section view of another embodiment to the invention. Here we see the surface elements 1A, 1B, and 1C with insulative portions 2, 2', and 2" as before. Now in this geometry there are two thermometric independent conductors 5A and 5B which are run inside of the catheter and, of course, insulated from each other over the entire length, except for the junction point 4 where they meet at the surface of the electrical contact 1A. There may be yet another conductor 1, not shown, which runs the entire length of the catheter and provides the voltage V from a source 3 as shown in FIG. 1. In this configuration, the two thermometric connections 5A and 5B could be copper and constantan, and still they meet at the surface to give a faithful, fast-acting thermocouple readout just where you want it, namely at the surface of the electrical contact 1A.

Figure 3:
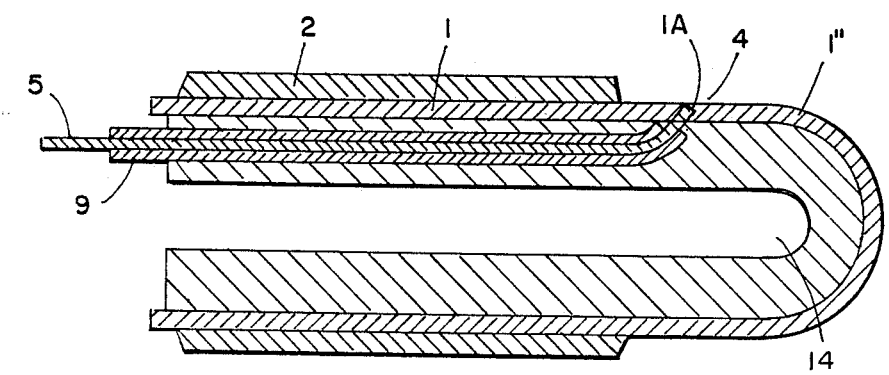
FIG. 3 shows a further embodiment of the electrode with a single thermocouple wire joining to a surface region of the catheter electrode tip.

FIG. 3 shows the type of geometry which was illustrated in FIG. 1, only in a bit more detail. Here we only have one surface electrode for illustration designated as 1". It is connected to a conductive element which runs the length of the catheter designated as 1. This could be a helical, stainless steel, or other metal, coil helix that goes the entire length of the catheter and ends up terminating on surface 1', and in fact being integral with 1'. Alternatively, it could be a separate conductive wire that is buried within the insulation 2 and runs the length of the catheter structure and makes electrical contact with surface area 1''. The thermometric conductor 5 is insulated by insulation 9 and runs the length of the catheter to terminate at the junction 4 at the surface of the electrode 1A. This is a simplified kind of thermocouple junction, as it involves only one thermometric carrier 5. This carrier could be, for example, constantan, and the entire electrical conveyance 1 could be stainless steel, making a stainless steel and constantan junction. The simplicity of this geometry in FIG. 3 is ideal for rugged and easily-configured tip. It would require only one thermometric line 5 in a helical or otherwise simplified catheter with a single electrical conductor 1. Of course, this geometry could be devised with multiple electrodes; each one of the electrode contacts could have thermometric reading.

One of the important features of this construction beyond its simplicity of fabrication is the fact that it gives faithful and rapid temperature reading just where you want it; namely, the place where you are making the temperature reading in the tissue. Because the electrical junction, for example in FIG. 3, designated as 4, is exactly at the surface of the electrical surface 1A means that you have no thermal mass effects at the tip, and the temperature that you read is precisely the temperature of the adjacent tissue outside of the electrode. In the cardiac application, the electrode surface will be used for heating via radiofrequency current which emanates from the surface as produced by the voltage source 3 in FIG. 1. The burst of energy from the radiofrequency source may be rapid, and the heating also very rapid. Thus you want extremely rapid temperature measurement to prevent unwanted damage to tissue or unfaithful recording of temperature in a critical temperature region. One of the reasons why the construction, as shown in this invention, is so important is that it gives you the best possible thermometric reading just where you want it at the surface of the electrode. It is also important to note that the thermocouple junctions can be extremely small yet rugged in construction, meaning that they have very little thermal mass and thus will not affect the temperature reading of the tissue which you wish to measure.

There are many other orientations, configurations, and embodiments of this general concept. In particular, the thermocouple or temperature measuring conductor 5 could be embedded within the insulation 2 of the entire catheter. It could also be helicly wound with the electrical conductor 1 over the entire length of the catheter. These two elements, 1 and 5, could be insulated from each other over the length of the catheter to prevent unwanted thermocouple junctions except at the very tip and where the measurement should be made. In the case of cardiac catheters, it is most important that the entire structure be very rugged and simple. This is one of the ideal features of the thermocouple construction because it is robust and still retains the flexibility that one needs in the cardiac application. One should also note that with these cardiac catheters, they are fed up through the vein in the groin to the cardiac region by a very stiff stylet. The stylet is often used to retain the tip of the electrode against the desired tissue wall for recording or, in this case, radiofrequency ablation. Thus, with the design shown here, all of the critical thermometric wires could be embedded in the wall and thus not perturb the inner stylet for the job that it must do. It would also be such that the stylet would not mechanically perturb or destroy these important thermometric and radiofrequency-carrying conductors.

We have been discussing this catheter in terms of radiofrequency heating, but the heating could be done in other ways. It could be resistive heating by other elements in the catheter or could be done with other frequency ranges of electrical current. In any case, the thermocouple junction concept, as described, still pertains and has the merits described above.

One of the features of the cardiac catheter which is important in some applications is the lumen, which is shown as 16 in FIG. 1, 12 in FIG. 2, and 14 in FIG. 3. This would be used for insertion of the introducing stylet to work the flexible catheter up into the body. The electrical wires, shown as 1 and 5 in FIG. 4, could be buried in the wall of this catheter and not be inside of the lumen. They could potentially be inside of the lumen if the structure were so arranged that the stylet could also be introduced for manipulation of the catheter. The presence of the lumen, however, is important in the sense that it is needed for introducing a stylet. This is one of the features of the cardiac electrode which has classically been used and is shown in the embodiments in FIGS. 1, 2, and 3. However, one can also have a similar flexible cardiac catheter with no lumen inside it, but with sufficiently stiff nature that it could be directed into the heart intravenously. We claim this embodiment in this invention, although it is not shown in the Figures.

As a technical note, one usually refers to the distal end of such catheter as the far end that is the most extremely into the body, and the proximal end, which is closest to the surgeon, that is out of the body.

It is also worth noting that there are many variations on the embodiments shown in FIGS. 1, 2, and 3 that are possible for those skilled in the art. The conductive elements as they are embedded in the insulating wall 2 could have a number of geometries, including spiral, helices, or just straight wire elements, and they could be preinsulated wires of various materials as discussed above. Also, the wall of the catheter itself could be made in a variety of ways, including fiber-impregnated tubing, or could be an integral structure of an insulative material. The conductors mentioned above could be wrapped over such an insulated core, and an insulation layer placed on top of that assembly. Polyurethane coatings are common in this application. The lumen, for example, in number 12 in FIG. 2 could go all the way through the catheter and actually have a front-facing, open end at the distal end. The number of electrical contacts could be great, far more than shown in the figures. Each one of those could have their own electrical contact for recording and stimulation, even for radiofrequency heating and temperature control as discussed in this patent.

Having described in detail various embodiments of my invention, what I claim and desire to secure by letters patent in the U.S. Patent Office are the following:

1. An electrode catheter system with temperature control adapted for making radiofrequency heat lesions in a body and particularly the cardiac region and having built-in thermocouple temperature sensor which can sense the temperature of the heated body tissue, said electrode having the shape of a elongated catheter with a distal end that is intended to be directed into the bodily tissue, particularly near the cardiac region to be heated, and a proximal end which is adapted to be connected to an external source of radiofrequency energy and to an external thermocouple temperature monitoring apparatus through a connection means, a portion of the elongated catheter electrode that will be inserted into the body comprising a flexible, tubular structure with an internal lumen and having a longitudinally extending insulating material portion, said electrode having at least one uninsulated conductive tip at its distal end from which, when in use, radiofrequency current will flow to heat surrounding tissue, said electrode having conductive means connecting said uninsulated distal tip to said connection means located near said proximal end of said electrode adapted for connection to an external source of radiofrequency potential, and whereby said internal lumen can be used to insert stylet means so that said catheter can be tunneled deep within the body through blood vessels, whereby when in use, said uninsulated tip will be at said radiofrequency potential, said electrode having a first metal element and a second metal element, both metal elements running from said proximal end to said distal end of said electrode, said two metal elements being the two sides of a thermocouple pair, said two metal elements being embedded within said longitudinally extending insulating material portion and electrically insulated from each other over the length of said electrode except at said distal end, the distal ends of said two metal elements being electrically fused at said distal end of said electrode to form a thermocouple junction in such a way that a portion of each of said distal ends of said two metal elements and a portion of said fused junction are part of an external surface of said uninsulated tip, the proximal ends of said two metal elements near the proximal end of said electrode are so adapted to be connected to an external thermocouple junction potential measuring apparatus; whereby, when in use, said electrode is inserted into the living body by inserting a stylet into said lumen means within said catheter-shaped electrode, and thus said distal end of said electrode can be worked into the proper position within the blood-carrying structure of the living body, once in position so described, the radiofrequency potential of said uninsulated tip of said electrode will cause a current to flow in and thus heat up the tissue surrounding said uninsulated tip, and said distal portions of said two metal elements and said portion of thermocouple junction which are on the external surface of said uninsulated tip will provide an intimate thermal contact with the heated tissue adjacent to said external surface and thus a reliable measure of the temperature of said adjacent tissue.

2. The electrode of claim 1 wherein said conductive means connecting said uninsulated tip of said rf connection means, a portion of said uninsulated conductive tip and one of said metal thermocouple elements are the same continuous metal structure.

3. The electrode of claim 2 wherein said embedded two metal thermocouple elements are insulated from external contacts from outside of the electrode except at the distal tip and insulated from the internal lumen of the electrode, such that when an insertion stylet is placed within the lumen for insertion of the electrode within the body, said stylet will not contact electrically or mechanically said two metal thermocopule elements.

4. An electrode catheter system with temperature control adapted for making radiofrequency heat lesions in a body and particularly the cardiac region and having built-in thermocouple temperature sensor which can sense the temperature of the heated body tissue, said electrode having the shape of a elongated catheter with a distal end that is intended to be directed into the bodily tissue, particularly near the cardiac region to be heated, and a proximal end which is adapted to be connected to an external source of radiofrequency energy and to an external thermocouple temperature monitoring apparatus through a connection means, a portion of the elongated catheter electrode that will be inserted into the body comprising a flexible structure having a longitudinally extending insulating material portion, said electrode having at least one uninsulated conductive tip at its distal end from which, when in use, radiofrequency current will flow to heat surrounding tissue, said electrode having conductive means connecting said uninsulated distal tip to said connection means located near said proximal end of said electrode adapted for connection to an external source of radiofrequency potential, and whereby said catheter can be tunneled deep within the body through blood vessels, whereby when in use, said uninsulated tip will be at said radiofrequency potential, said electrode having a first metal element and a second metal element, both metal elements running from said proximal end to said distal end of said electrode, said two metal elements being the two sides of a thermocouple pair, said two metal elements being embedded within said longitudinally extending insulating material portion and electrically insulated from each other over the length of said electrode except at said distal end, the distal ends of said two metal elements being electrically fused at said distal end of said electrode to form a thermocouple junction in such a way that a portion of each of said distal ends of said two metal elements and a portion of said fused junction are part of an external surface of said uninsulated tip, the proximal ends of said two metal elements near the proximal end of said electrode are so adapted to be connected to an external thermocouple junction potential measuring apparatus; whereby, when in use, said electrode is inserted into the living body, and thus said distal end of said electrode can be worked into the proper position within the blood-carrying structures of the living body, once in position so described, the radiofrequency potential of said uninsulated tip of said electrode will cause a current to flow in and thus heat up the tissue surrounding said uninsulated tip, and said distal portions of said two metal elements and said portion of thermocouple junction which are on the external surface of said uninsulated tip will provide an intimate thermal contact with the heated tissue adjacent to said external surface and thus a reliable measure of the temperature of said adjacent tissue.

* * * * *